US012125594B2

United States Patent
Jirsa et al.

(10) Patent No.: US 12,125,594 B2
(45) Date of Patent: Oct. 22, 2024

(54) METHOD FOR DETERMINING AN ONSET TIME AND AN EXCITABILITY OF A BRAIN REGION

(71) Applicants: UNIVERSITÉ D'AIX-MARSEILLE (AMU), Marseilles (FR); INSTITUT NATIONAL DE LA SANTÉ ET DE LA RECHERCHE MÉDICALE, Paris (FR)

(72) Inventors: Viktor Jirsa, Marseilles (FR); Viktor Sip, Marseilles (FR)

(73) Assignees: UNIVERSITÉ D'AIX MARSEILLE (AMU), Marseilles (FR); INSTIT NAT DE LA SANTÉ ET DE LA RECHERCHE MÉDICALE, Paris (FR)

( * ) Notice: Subject to any disclaimer, the term of this patent is extended or adjusted under 35 U.S.C. 154(b) by 394 days.

(21) Appl. No.: 17/625,204

(22) PCT Filed: Jul. 22, 2020

(86) PCT No.: PCT/EP2020/070717
§ 371 (c)(1),
(2) Date: Jan. 6, 2022

(87) PCT Pub. No.: WO2021/013902
PCT Pub. Date: Jan. 26, 2021

(65) Prior Publication Data
US 2022/0262515 A1    Aug. 18, 2022

(30) Foreign Application Priority Data
Jul. 22, 2019   (EP) .................................... 19187615

(51) Int. Cl.
*G06F 17/00*    (2019.01)
*A61B 6/00*    (2006.01)
(Continued)

(52) U.S. Cl.
CPC ........... *G16H 50/20* (2018.01); *A61B 6/5217* (2013.01); *G16H 50/50* (2018.01)

(58) Field of Classification Search
CPC ....... G16H 50/20; G16H 50/50; A61B 6/5217
See application file for complete search history.

(56) References Cited

U.S. PATENT DOCUMENTS 8,725,243 B2 * 5/2014 Dilorenzo .............. A61B 5/024
600/544
8,868,172 B2 * 10/2014 Leyde .................... G16H 20/10
600/544

(Continued)

FOREIGN PATENT DOCUMENTS

| EP | 3235427 A1 | 10/2017 |
|---|---|---|
| WO | 2018015778 A1 | 1/2018 |
| WO | 2019094836 A1 | 5/2019 |

OTHER PUBLICATIONS

Naze et al, Computational Modeling of Seizure Dynamics Using Coupled Neuronal Networks: Factors Shaping Epileptiform Activity, PLOS Computational Biology, Institut de Neurosciences des Systèmes, Marseille, France, 2 Aix-Marseille University, Marseille, France, 21 pages (Year: 2015).*

(Continued)

*Primary Examiner* — Mohammed H Zuberi
(74) *Attorney, Agent, or Firm* — Seckel IP, PLLC (57) ABSTRACT

The method for determining an onset time and an excitability of a brain region that is not observed as recruited or not recruited in a seizure activity of an epileptic patient brain includes: providing a dynamical model of a propagation of an epileptic seizure in the brain networks; providing a statistical model which defines the probability of generating sets of observations of the state of the brain networks by said dynamical model; training the dynamical model of the propagation of an epileptic seizure using the statistical (Continued)

model and the data set of observations of the training cohort; and inverting the trained dynamical model and inferring the onset time and excitability of a third region from the onset time that is observed for the first and second regions using the statistical model.

20 Claims, 8 Drawing Sheets

(51) Int. Cl.
  *G16H 50/20* (2018.01)
  *G16H 50/50* (2018.01)

(56) References Cited

U.S. PATENT DOCUMENTS

| | | | | |
|---|---|---|---|---|
| 9,415,222 | B2* | 8/2016 | DiLorenzo | A61B 5/1114 |
| 9,643,019 | B2* | 5/2017 | Higgins | G16H 40/67 |
| 11,076,799 | B2* | 8/2021 | Hecox | A61B 5/7203 |
| 11,103,193 | B2* | 8/2021 | Behnam | A61B 5/30 |
| 2002/0035338 | A1* | 3/2002 | Dear | A61B 5/369 |
| | | | | 600/544 |
| 2004/0054297 | A1* | 3/2004 | Wingeier | A61B 5/165 |
| | | | | 600/544 |
| 2019/0142338 | A1 | 5/2019 | Fang et al. | |
| 2019/0223779 | A1 | 7/2019 | Mersmann et al. | |
| 2019/0254585 | A1 | 8/2019 | Jirsa et al. | |
| 2020/0368491 | A1* | 11/2020 | Poltorak | A61N 1/0456 |
| 2021/0169411 | A1 | 6/2021 | Fang et al. | |

OTHER PUBLICATIONS

Golos et al, Multistability in Large Scale Models of Brain Activity, PLOS Computational Biology, Aix-Marseille Université, Inserm, INS UMR_S 1106, Marseille, France, 2 Ecole Centrale Marseille, Marseille, France, 32 pages (Year: 2015).*
Schirner et al, Inferring multi-scale neural mechanisms with brain network modelling, elifesciences.org, Aug. 1, 2018, 30 pages (Year: 2018).*
Proix et al, Predicting the spatiotemporal diversity of seizure propagation and termination in human focal epilepsy, Nature Communications, 15 pages (Year: 2018).*
Zorgno et al, Epilepsy seizure onset detection applying 1-NN classifier based on statistical parameters, IEEE Biennial Congress of Argentina, 5 pages (Year: 2018).*
Usman et al, Epileptic Seizures Prediction Using Machine Learning Methods, Computational and Mathematical Methods in Medicine vol. 2017, 10 pages (Year: 2017).*
International Search Report and Written Opinion dated Oct. 22, 2020 in counterpart application No. PCT/EP2020/070717; in English (total 11 pages).
JP Office Action dated Aug. 28, 2024 in counterpart application No. JP 2022-518307; with machine translation (total 14 pages) (note: EP3235427 cited in the JP Office Action is not listed in this IDS since its already of record in this application).

* cited by examiner

METHOD FOR DETERMINING AN ONSET TIME AND AN EXCITABILITY OF A BRAIN REGION

FIELD OF THE INVENTION

The invention relates to a method for determining an onset time and an excitability of a brain region that is not observed as recruited or not recruited in a seizure activity of an epileptic patient brain.

BACKGROUND OF THE INVENTION

A possible treatment for patients with medically refractory epilepsy is a surgical intervention aimed at the removal of one or more suspected epileptogenic zones, i.e. brain regions responsible for the initiation of the seizures. However, these surgical interventions have success rates at only 60-70%.

Such success rates may be increased however, using the method disclosed in the document WO2018/015778A1. This document discloses a method of modulating epileptogenicity in a brain of an epileptic patient comprising the steps of: providing a virtual brain; providing a model of an epileptogenic and of a propagation zones and loading said models in the virtual brain to create a virtual epileptic brain; acquiring data of the brain of the epileptic patient; identifying, in said data, a location of at least one possible epileptogenic zone; fitting the virtual epileptic brain against the data acquired from the epileptic patient and parametrizing said at least one possible epileptogenic zone in the virtual epileptic brain as an epileptogenic zone; and simulating, within the virtual epileptic brain, the effect of a network modulation mimicking a clinical intervention of the brain of the patient. Mimicking a clinical intervention of the brain of the patient may, in turn, allow to define improved strategies for surgery and increase the low success in the surgical interventions.

In fact, low success rates in surgical operations are, in most cases, attributed to a failure to the localization of the epileptogenic zone, which is partly attributed to the incomplete picture of the whole-brain seizure propagation patterns caused by the insufficient spatial sampling. Indeed, the current standard in pre-surgical evaluation is the use of either implanted depth electrodes (stereo-electroencephalography, SEEG) or subdural electrode grids. None of these methods allows for the exploration of the whole brain, and they are typically limited to the regions suspected to be part of the epileptogenic network based on the non-invasive evaluation.

Computer-aided methods aiming at the improvement in surgical planning avoid this insufficient spatial sampling assuming that the relevant targets of possible resection are among the regions explored by the electrodes implantation. In such cases, the behaviour of the rest of the brain network is not taken into account. Some of these methods are based on analysis of the recorded signals using spectral or temporal features. Other of these methods are based on the analysis of functional networks derived from the intracranial recordings.

The known methods that model the activity in the whole brain network, and not just the explored subnetwork require some manual tuning of the model settings, often in terms of the epileptogenic zone hypothesis specified by the clinical expert and thus cannot be utilized fully automatically.

SUMMARY OF THE INVENTION

According to a first aspect, the invention concerns A method for determining an onset time and/or an excitability of a brain region that is not observed as recruited or not observed as not recruited in a seizure activity of an epileptic patient brain, comprising the steps of:

providing computerized brain networks, said networks modelling various regions of a brain and connectivity between said regions for a training cohort of epileptic patients brains and for the patient brain;

providing data sets of observations of the state of the brain networks during epileptic seizure for the training cohort and for the patient brain, said observations defining regions in the brain networks as first regions that are observed as recruited in an epileptic seizure activity of the patient brain at an onset time, second regions that are observed as not recruited in said epileptic seizure activity of the patient brain, and third regions that are either not observed as recruited or not observed as not recruited in said seizure activity of the patient brain;

providing a dynamical model of a propagation of an epileptic seizure in the brain networks;

providing a statistical model which defines the probability of generating said sets of observations of the state of the brain networks by said dynamical model;

training the dynamical model of the propagation of an epileptic seizure using the statistical model and the data set of observations of the training cohort; and inverting the trained dynamical model and inferring the onset time and/or excitability of a third region from the onset time that is observed for the first and second regions using the statistical model.

Preferentially, —wherein the onset time and the excitability of the third region are inferred; —the computerized brain networks are obtained from magnetic resonance neuroimaging and/or diffusion-weighted magnetic resonance imaging data; —the data sets of observations of the state of the brain networks during epileptic seizure are obtained by running a seizure onset detection algorithm on intracranial electroencephalography signals and by mapping these detected onset times to the regions of the brain network; —the seizure onset detection algorithm employs the time-frequency analysis of the intracranial electroencephalography signal; —the mapping of the onset times detected in the intracranial electroencephalography signals onto the brain regions is based on the physical distance of the electrode contact from which the signal is recorded and the brain region; —the dynamical model describes an evolution of a slow variable of a single region of a network by an activation function, which is a function of the excitability of the region and of the network effects, and wherein the region onset time is defined as the time when the slow variable crosses a given threshold; —the training of the dynamical model equates to finding the optimal set of parameters of the activation function; the parameters of the activation function of the dynamical model and the region excitabilities and onset times are inferred by an Hamiltonian Monte Carlo method; —the dynamical model of a propagation of an epileptic seizure in the brain network is defined, for a brain network with n regions, by the equation as follows:

$$\dot{z}_i = f_q\left(c_i, \sum_{j=1}^{n} w_{ij} H(z_j - 1)\right)$$

for $i = 1, \ldots, n$ $z_i(0) = 0$ wherein the function $f_q: \mathbb{R} \times [0; \overline{T}] \to \mathbb{R}+$ is the activation function, $c_i$ is a node excitability and $W=(w_{ij})$ is a connectivity matrix, normalized so that $\max_i \Sigma_j q_{ij}=1$ and H is the Heaviside step function representing the switch from an healthy to seizure state when the slow variable cross the threshold z=1; —the statistical model is a hierarchical model built on the principles of Bayesian inference, where the top level parameters are the parameters of the activation function and the bottom level parameters are the region excitabilities; —the statistical model includes an assumption that the excitabilities of all regions for all training data have the same prior distribution; —the function f is a bilinear function followed by an exponentiation, and the parameters of the function are the values of the function f in four specified points in $\mathbb{R} \times [0; \bar{t}\,]$; —the statistical model is such as $q_{11}, q_{12} \sim \text{Normal}(0, \sigma_q)$
$q^*_{21}, q^*_{22} \sim \text{HalfNormal}(0, \sigma_q)$
$q = (q_{11}, q_{12}, q_{11} + q^*_{21}, q_{12} + q^*_{22})$
For $k = 1, \ldots, n_{seizures}$:
$\quad c_k \sim \text{Normal}(0, 1)$
$\quad t_k = P(c_k, q, W_k)$
$\quad \bar{t}_{k, seizing} \sim \text{Normal}(\min(t_{k, seizing}, t_{lim}), \sigma_t)$
$\quad t_{lim} \sim \text{Normal}(\min(t_{k, nonseizing}, t_{lim}), \sigma_t)$ wherein $\bar{t}_{k, seizing}$ are the observed onset times of seizing nodes, $\sigma q = 30$, $\sigma_t = 5$ s, $t_{lim} = 90$ s, and $P(c_k, q, W_k)$ represents the dynamical model, mapping the excitabilities $c_k$, parameters q, and the connectome matrix $W_k$ onto the onset times $t_k$.

BRIEF DESCRIPTION OF THE DRAWINGS

Other features and aspects of the present invention will be apparent from the following description and the accompanying drawings, in which.

DETAILED DESCRIPTION OF THE INVENTION

The invention concerns a method for determining an onset time and/or an excitability of a brain region that is not observed as recruited or not observed as not recruited in a seizure activity of an epileptic patient brain. It relates to a method which attempts to infer the activity of the whole brain network during a seizure from the activity of the observed brain subnetwork and from the structural connectome. The method is based on the assumption that the activity in any brain region can be categorised as either a normal state or a seizure state, and that the time of the change between these states (region onset time) is the only relevant feature for the inference of the propagation pattern.

The method works in two phases. In the training phase, the global parameters of the model, i.e. those shared among different subjects and seizures, are inferred from the training data. In the application phase the trained model is applied to a single seizure data, and the activity in the whole brain network is inferred for the seizure. Thanks to this data-driven approach, only few clearly interpretable constants have to be specified, and no manual tuning is therefore necessary on the global or patient-specific level.

Figure 1:
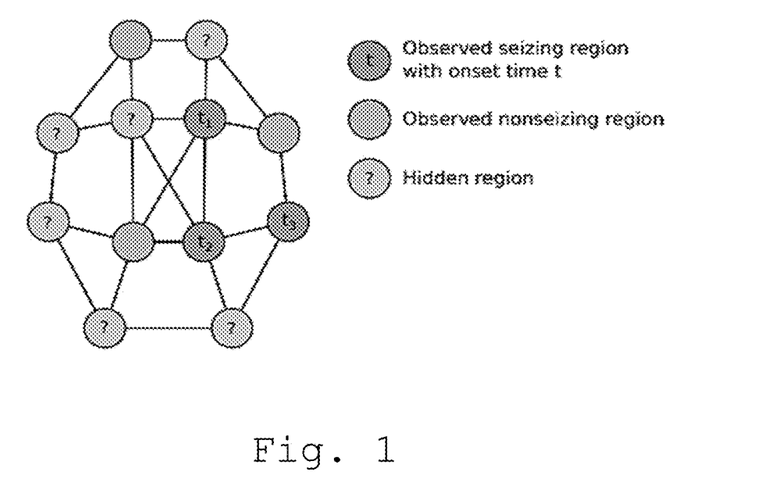
FIG. 1 is a schematic overview of the problem of seizure propagation inference according to the invention.

As shown in FIG. 1, the state of a brain network during an epileptic seizure evolution is known only partially. Some brain regions are observed and participating in the seizure activity with onset times $t_i$. Other brain regions are observed but not participating in the seizure activity. And still other regions are not observed, but are hidden, i.e. it is not known whether they participate in the seizure activity or not. These are the brain regions that are not observed as recruited or not recruited in a seizure activity of an epileptic patient brain.

Figure 2:
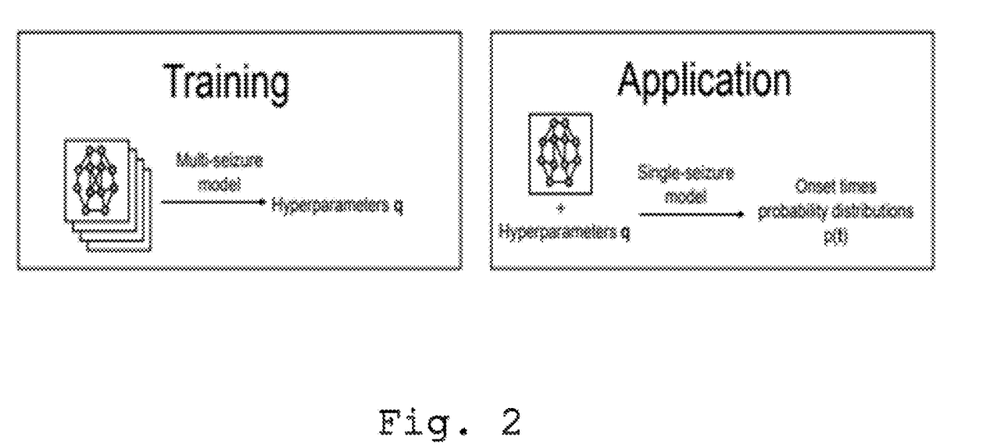
FIG. 2 illustrates the training and application phases according to the method of the invention.

As shown in FIG. 2, the method of the invention allows to infer the state of the hidden nodes using the structural connectivity known from diffusion-weighted imaging. (Bottom) Two-phases of the inference. In the training phase, the hyperparameters of the model are learned from the training data. In the application phase, the model is applied to a single seizure.

For the implementation of the method of the invention, computerized brain networks are provided. These networks are modelling various regions of a brain and connectivity between said regions for a training cohort of epileptic patients brains and for the patient brain. The computerized brain networks are obtained from magnetic resonance neuroimaging and/or diffusion-weighted magnetic resonance imaging data. Also, data sets of observations of the state of the brain networks during epileptic seizure are provided for a training cohort and for the patient brain, said observations defining regions in the brain networks as first regions that are observed as recruited in an epileptic seizure activity of the patient brain at an onset time, second regions that are observed as not recruited in said epileptic seizure activity of the patient brain, and third regions that are either not observed as recruited or not recruited in said seizure activity of the patient brain.

These form input data, that thus comprise connectome matrices. The computerized brain networks are obtained from magnetic resonance neuroimaging and/or diffusion-weighted magnetic resonance imaging data. The individual structural connectome matrices are obtained, for example, from patient T1 and diffusion-weighted MRI scans using existing known available software. The methods for the connectome reconstruction are generally known in the field.

These input data also comprise regions onset times. These is the information if and when regions enter the seizure state. In order to obtain such information data, the steps as followed are carried out:

first, intracranial seizure recordings are provided and, in each bipolar channel, onset times are detected by evaluating when the signal power crosses a given threshold. Specifically, the whitened power in the band [4, 60] Hz and a threshold of log ratios equal to 2, relative to the preictal baseline, are used. It is noted that other implementations are however possible, either using different frequency bands, or using other approaches, such as detection methods based on machine learning.

second, all bipolar channels are assigned to brain regions. For each channel, it is selected the closest brain region, as determined by the volume parcellation provided by the known FreeSurfer™ software and the position of the electrode contacts determined from CT scans of the brain with implanted electrodes. If there are multiple regions close to the contact, having a distance ratio <2, the regions are not assigned and the information from the channel is not used.

third, the regions with no assigned channel are marked as hidden. For the regions with one assigned channel the detected channel onset time is used as the region onset time. If multiple channels are assigned to one region, the median of the detected onset times is taken.

According to the invention, a dynamical model of the recruitment and the epileptic seizure propagation in the brains networks is provided. The dynamical model describes an evolution of a slow variable of a single region of a network by an activation function, which is a function of the excitability of the region and of the network effects, and wherein the region onset time is defined as the time when the slow variable crosses a given threshold.

For a network having n regions, the model is defined by the equation (1) as follows:

$$\dot{z}_i = f_q\left(c_i, \sum_{j=1}^{n} w_{ij} H(z_j - 1)\right) \quad (1)$$

for $i = 1, \ldots, n$

In this equation $z_i$ is the slow variable of region i, analogous to the slow variable in the Epileptor model (Jirsa, V., Stacey, W., Quilichini, P., Ivanov, A., Bernard, C., jul 2014. On the nature of seizure dynamics. Brain 137 (8), 2110-2113). The function $f_q: \mathbb{R} \times [0:1] \to \mathbb{R}+$ is the activation function, parameterized by the parameter vector q. Function $f_q$ is increasing w.r.t. its first parameter. Parameter $c_i$ is the node excitability, and $W=(w_{ij})$ is the connectivity matrix, normalized so that $\max_i \Sigma_j w_{ij}=1$. Finally, H is the Heaviside step function, representing the switch from the healthy to seizure state when the slow variable cross the threshold z=1. The onset time of a region i is defined as $t_i=\min\{t | z_i(t) \geq 1\}$. The system is completed by the initial conditions $z_i(0)=0$.

Because the function $f_q$ is positive, this model implies that every region will start to seize at some finite time. In reality, this is not the case, and to account for that in the statistical model it is introduced a time limit of seizure, and it is considered all regions with onset time larger than the limit to be non-seizing.

For a known vector of excitabilities c, parameter vector q, and the connectome matrix W the model uniquely defines the vector of onset times t. It is use the following shorthand for this mapping, corresponding to equation (2) hereunder:

$$P(c,q,W)=t \quad (2)$$

For the parametrization of the activation function $f_q$, the exponential bilinear function is used as the parameterization of $f_q(c, y)$. Parameterized by four coefficients $q=(q_{11}, q_{12}, q_{21}, q_{22})$ in the interpolation points $[c_a, y_a], [c_a, y_b], [c_b, y_a], [c_b, y_b]$ (with $c_a=-1, c_b=1, y_a=0, y_b=1$), the function is given by $$f_q(x, y) = \exp\left(\frac{1}{(c_b - c_a)(y_b - y_a)}(q_{11}(c_b - c)(y_i - y) + q_{23}(c - c_a)(y_b - y) + q_{12}(c_b - c)(y - y_a) + q_{22}(c - c_a)(y - y_a))\right)$$

In order to assure that f increases in c, it is placed additional constraints on the coefficients: $q_{21} > q_{11}$ and $q_{22} > q_{12}$.

The method according to the invention further comprises the steps of providing a statistical model which defines the probability of generating said sets of observations of the state of the brain networks by said dynamical model; and training the dynamical model of the propagation of an epileptic seizure using the statistical model and the data set of observations of the training cohort. This is the training phase. Training of the dynamical model equates to finding the optimal set of parameters of the activation function.

The statistical model is a hierarchical model that is for example built on the principles of Bayesian inference, where the top level parameters are the parameters of the activation function and the bottom level parameters are the region excitabilities. However, this is an example. The statistical model preferentially includes an assumption that the excitabilities of all regions for all training data have the same prior distribution.

In the training phase, data from multiple seizures are used to infer the optimal values of the parameter vector q, which is shared among all seizures. The statistical model for the model training is built the following way: it is assumed that for each seizure, the values of the excitability vector $c_k$, follow the standard normal distribution, and the activation function parameters q are treated as the hyperparameters of the model. Further, it is assumed that the observed onset times are measured imprecisely with standard deviation $\sigma_t$. Finally, to deal with the regions that do not seize, a limit $t_{lim}$ is set, and every region that seizes after this limit is treated as non-seizing. The full multi-seizure statistical model is shown below:

Input data: Connectome matrices $W_k$, sets of seizing and sets of nonseizing nodes, onset times of seizing nodes $\bar{t}_{k,seizing}$.

Parameters: $\sigma_q=30$, $\sigma_t=5$ s, $t_{lim}=90$ s

Model:
  $q_{11}, q_{12} \sim \text{Normal}(0, \sigma_q)$
  $q^*_{21}, q^*_{22} \sim \text{HalfNormal}(0, \sigma_q)$
  $q=(q_{11}, q_{12}, q_{11}+q^*_{21}, q_{12}+q^*_{22})$
  For $k=1, \ldots, n_{seizures}$:
    $c_k \sim \text{Normal}(0,1)$
    $t_k = P(c_k, q, W_k)$
    $\bar{t}_{k,seizing} \sim \text{Normal}(\min(t_{k,seizing}, t_{lim}), \sigma_t)$
    $t_{lim} \sim \text{Normal}(\min(t_{k,nonseizing}, t_{lim}), \sigma_t)$ This statistical model defines a posterior probability distribution for hyperparameters q and seizure-specific excitability parameters $c_k$. The samples from this probability distribution are drawn using the Hamiltonian Monte Carlo method using the sampler implemented in the Stan™ software. Since in this phase a point estimate for the hyperparameters q is wanted to be obtained, a median of all samples is taken for each component of the parameter vector.

The method according to the invention further comprises the step of inverting the trained dynamical model and inferring the onset time and/or excitability of a third region—in fact at least one of the third regions, or even all third regions—from the onset time that is observed for the first and second regions using the statistical model. This is the application phase. In this phase, the parameters of the activation function of the dynamical model and the region excitabilities and onset times are inferred by an Hamiltonian Monte Carlo method.

As concerns the application phase, once the parameters of the activation function $f_q$ are learned from a training batch of seizure data, the additional seizures can be processed one-by-one using a single-seizure model as follows:

Input data: Connectome matrix W, set of seizing and set of nonseizing nodes, onset times of seizing nodes $t_{seizing}$, parameters of the activation function q.
Parameters: $\sigma_q=30$, $\sigma_t=5$ s, $t_{lim}=90$ s
Model:
c~Normal(0,1)
t=P(c,q,W)
$\bar{t}_{seizing}$~Normal(min($t_{seizing}$,$t_{lim}$),$\sigma_t$)
$t_{lim}$~Normal(min($t_{nonseizing}$, $t_{lim}$),$\sigma_t$)

The model is a simplification of the multi-seizure model using the knowledge of the parameter vector q. Just as from the multi-seizure model, the samples from the posterior distribution of the singe-seizure model can be drawn using the Hamiltonian Monte Carlo method. The result of the single-seizure inference are the sampled excitabilities c and onset times t.

In this section we present results showing the performance of the method on synthetic data generated by the same model. These results that are obtained using the method according to the invention demonstrate that if the assumptions of the method are satisfied in the real epileptic networks, inference of the hidden states might be possible. Indeed, the invention allows to predict if a hidden region will seize or not. Additionally, if a hidden region seizes, the invention allows to predict when exactly. Finally, the invention allows to recover the region excitabilities.

Example 1: Testing Data

For the purposes of testing, synthetic data are generated by the same model as used for the inference. We have used connectome matrices from ten subjects are used, using the Desikan-Killiany parcellation, with 84 nodes. From these ten connectomes, two groups of ten seizures are generated, all of them with three different parameter set of the activation function: one for no coupling (q=(−5.0, −5.0, −3.0, −3.0)), one for weak coupling (q=(−6.5, −3.0, −3.5, 12.0)), and one for strong coupling (q=(−11.2, 5.3, −6.2, 69.3)). Finally, the number of observed regions are set to 21, 42, and 63 out of 84 regions in the parcellation. In total, this gives (2 groups)×(3 coupling strengths)×(3 numbers of observed regions)=18 groups, each with 10 seizures. For all cases, the excitabilities c are randomly drawn from standard normal distribution, and the observed nodes are selected randomly. The inference is run separately on each of the 18 groups.

Example 2: Results

Figure 3:
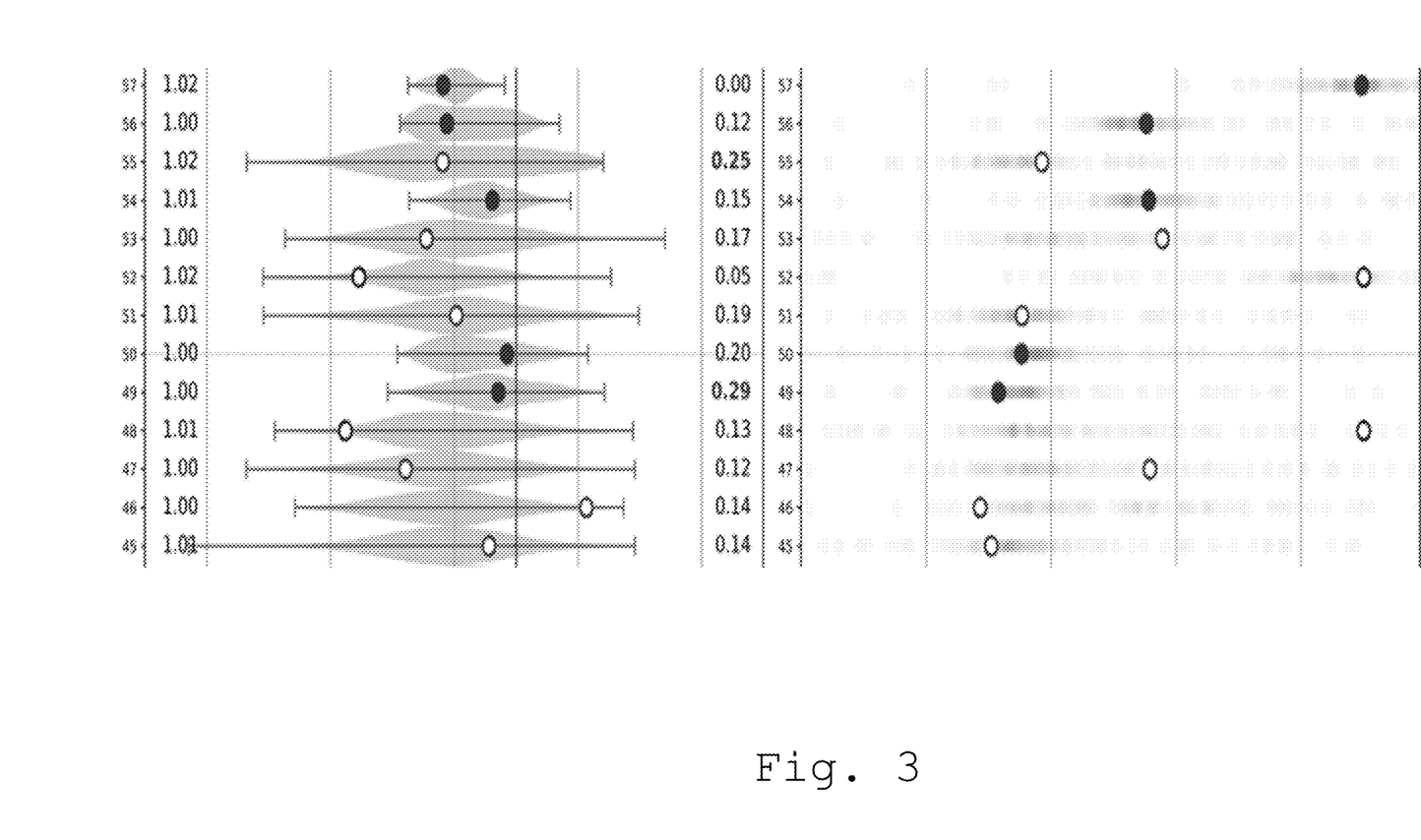
FIG. 3 shows the inference results for a single seizure with strong coupling and 21 observed regions, that are obtained according to the method of the invention.

Exemplary results of the inference for a single seizure are partially shown on FIG. 3, while the cumulative results from all tests are represented on FIGS. 4, 5, 6A, 6B, 6C, 7A, 7B and 7C.

In FIG. 3, an example of the inference results is partially shown for a single seizure with strong coupling and 21 observed regions. Left partial panel show the true (dots) and inferred (plots) excitabilities of the 84 brain regions. Full dots mark the observed regions, while empty-faced dots mark the regions that are hidden. Light-grey regions are those that seize, while dark-grey are those that do not. Numbers in the left column are the $\hat{R}$ diagnostic values. Numbers in the right column is the inferred probability p(c>1) which is equated with the probability that the node is epileptogenic. Right panel show the true (light-grey/dark grey dots) and inferred (grey dots) region onset times. Same rules for the full/empty and light grey/dark-grey dots apply as for the left panel. The results demonstrate that the onset time of the hidden nodes is in some cases inferred correctly.

Figure 4:
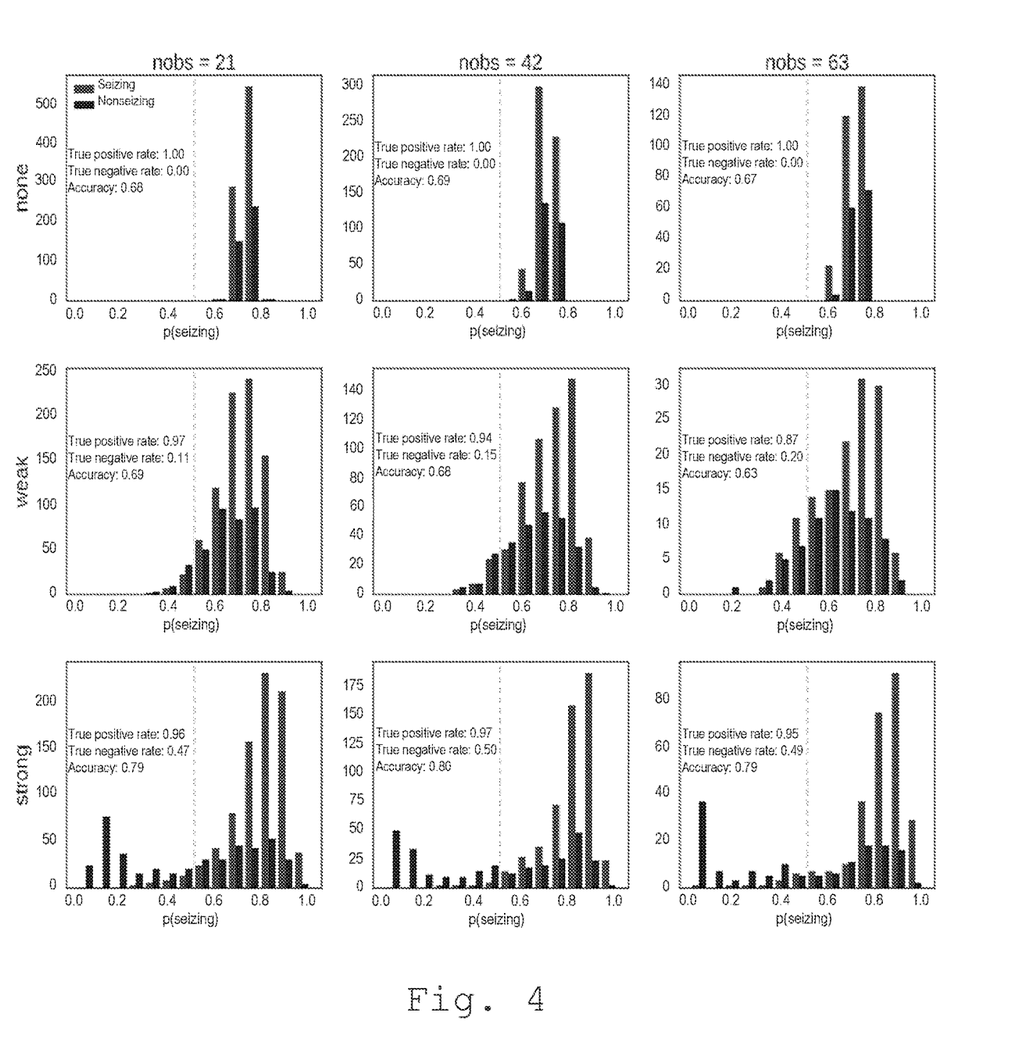
FIG. 4 illustrates the probability if seizing in the hidden nodes that is obtained according to an example of implementation of the method of the invention.

FIG. 4 illustrates how well one can predict if a hidden region seizes or not. It shows inferred probability of seizing activity in the hidden nodes. In the grid, the rows represent three different coupling strengths, and the columns represent different number of observed regions. Each panel in the grid represents the results of the inferences on two groups, each with ten subjects. Histogram counts the probability that a hidden region participates in the seizure activity. In light-grey is the histogram for the seizing nodes, and in dark-grey is the histogram for non-seizing nodes. The inset text show the measures of classification when the regions are classified as seizing or non-seizing based on the inferred probability with threshold equal to 0.5. The results show that seizing and Non-seizing nodes can be reliable distinguished only for strong coupling. The number of observed nodes (nobs) does not necessarily increase the classification quality.

Figure 5:
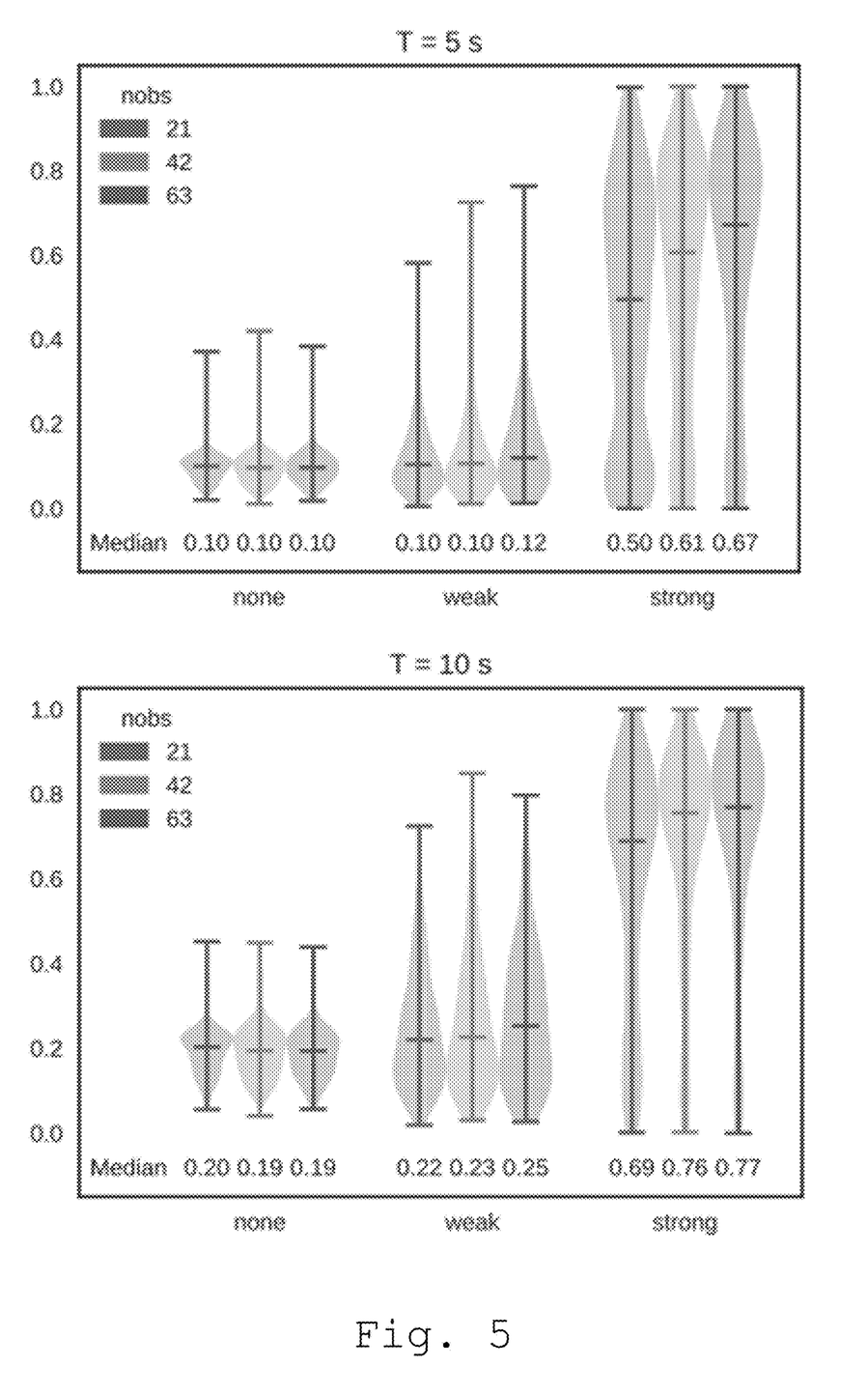
FIG. 5 illustrates the probability that the inferred onset time is within T seconds of the true onset time for hidden seizing regions according to the method of the invention.

FIG. 5 further illustrates how well can be the precise onset time estimated for the seizing regions. It shows the probability that the inferred onset time is within T seconds of the true onset time for hidden seizing regions. This probability is calculated for each hidden seizing region by counting fraction of the samples of the onset time in the window $[t_{true}-T; t_{true}+T]$. The results demonstrate that the onset time can be reliable inferred with strong coupling, and adding the observed nodes increase the precision further. On the other hand, with no coupling the number of the observed nodes does not change the prediction quality.

Figure 6A:
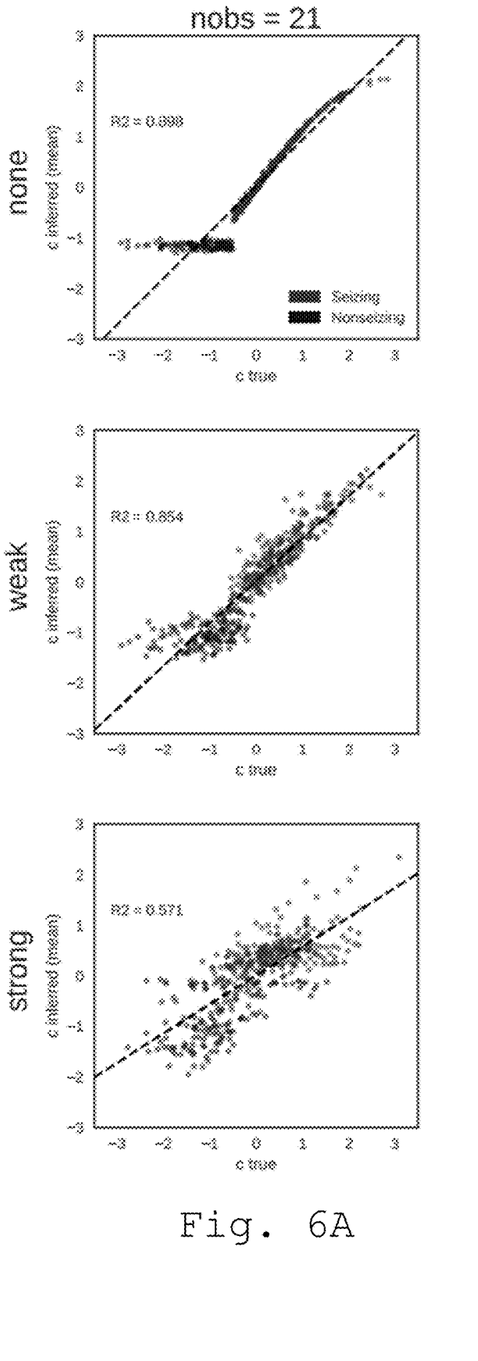
FIGS. 6A, 6B and 6C illustrate true and inferred region excitabilities for observed regions according to the method of the invention.
Figure 6B:
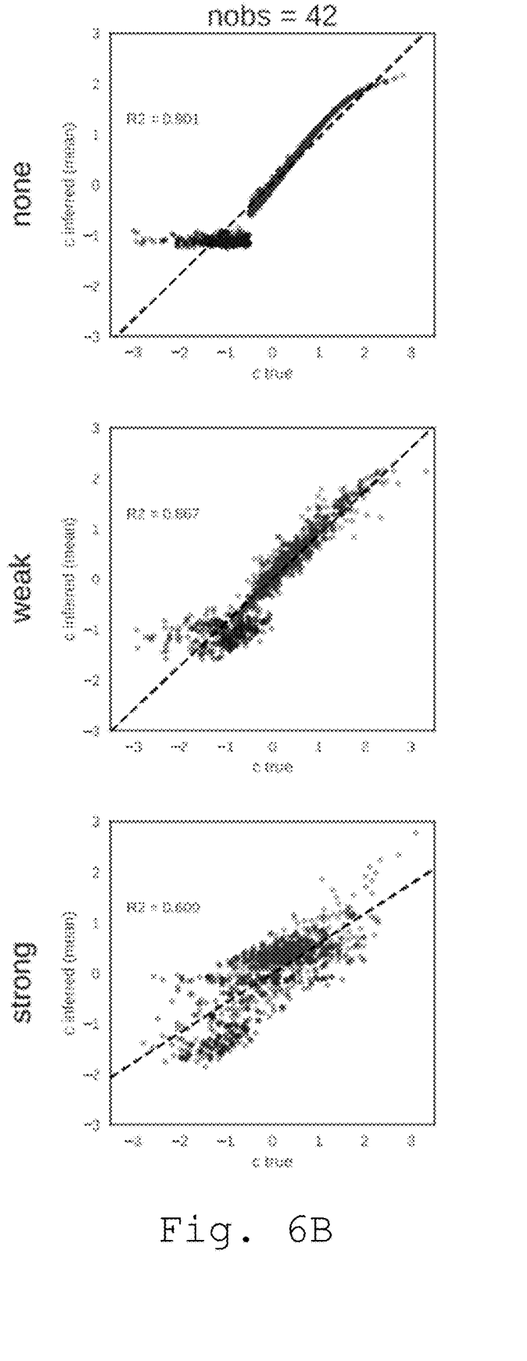
Figure 6C:
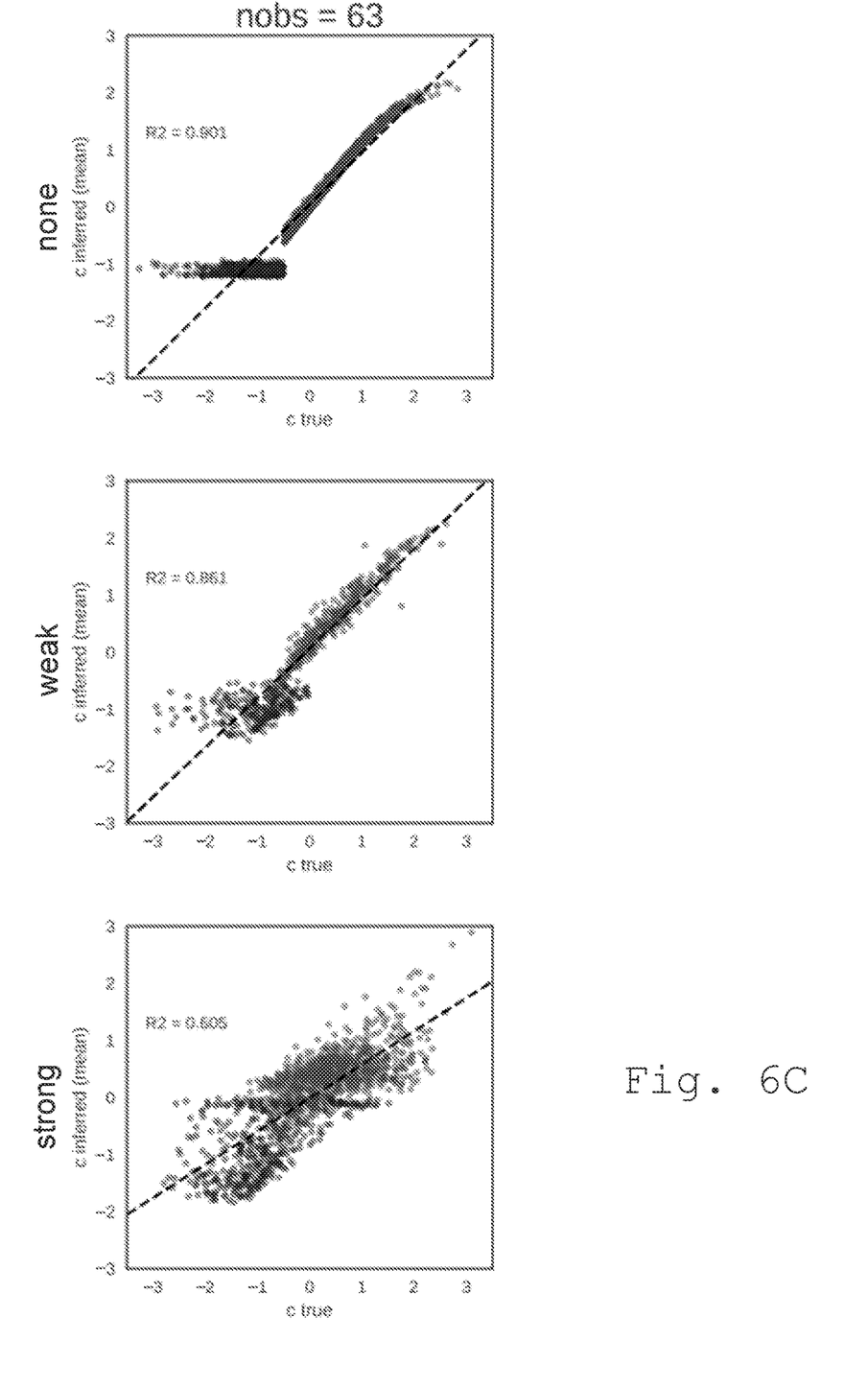

FIGS. 6A, 6B and 6C illustrate how the region excitabilities can be recovered for the nodes that are not observed. They show true and inferred region excitabilities for observed regions. In the grid, the rows represent three different coupling strengths, and the columns represent different number of observed regions. Each panel shows the true (x-axis) and mean inferred excitabilities (y-axis) for the seizing (in light-grey) and non-seizing (in dark-grey) regions. Perfect inference would have all dots along the diagonal. The inset number show the $R^2$ coefficient of the linear regression. The inference is very good with no coupling, when strong coupling is introduced, some precision is lost due to the network effects.

Figure 7A:
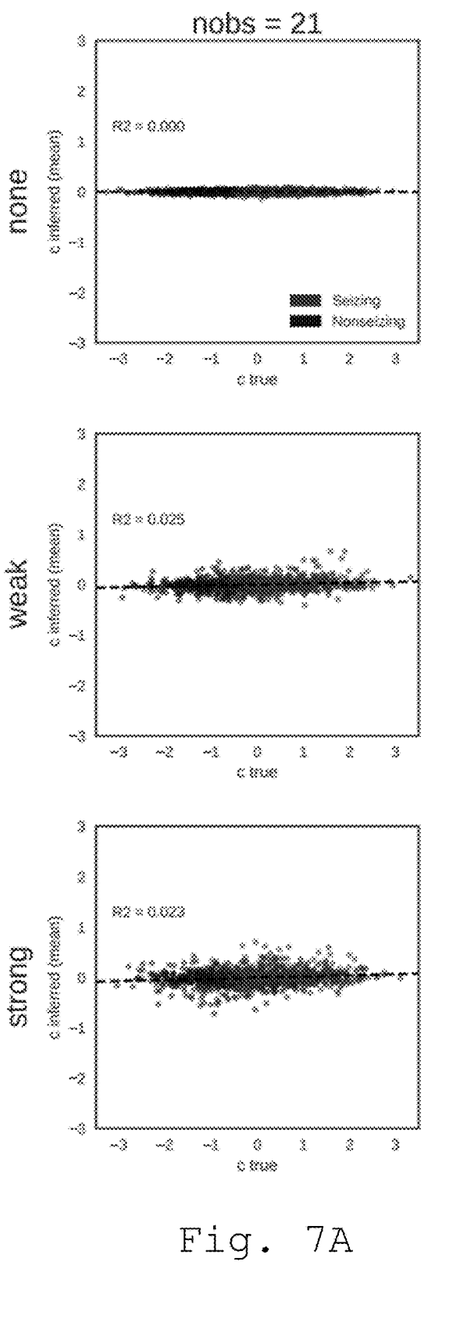
FIGS. 7A, 7B and 7C illustrate true and inferred node excitabilities for hidden regions according to the method of the invention.
Figure 7B:
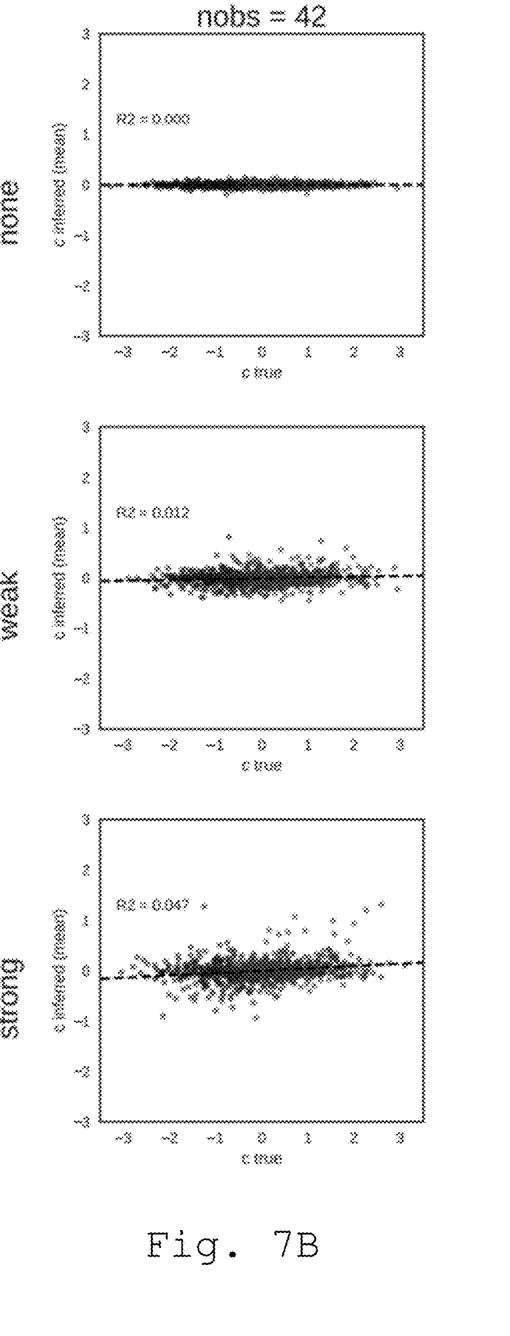
Figure 7C:
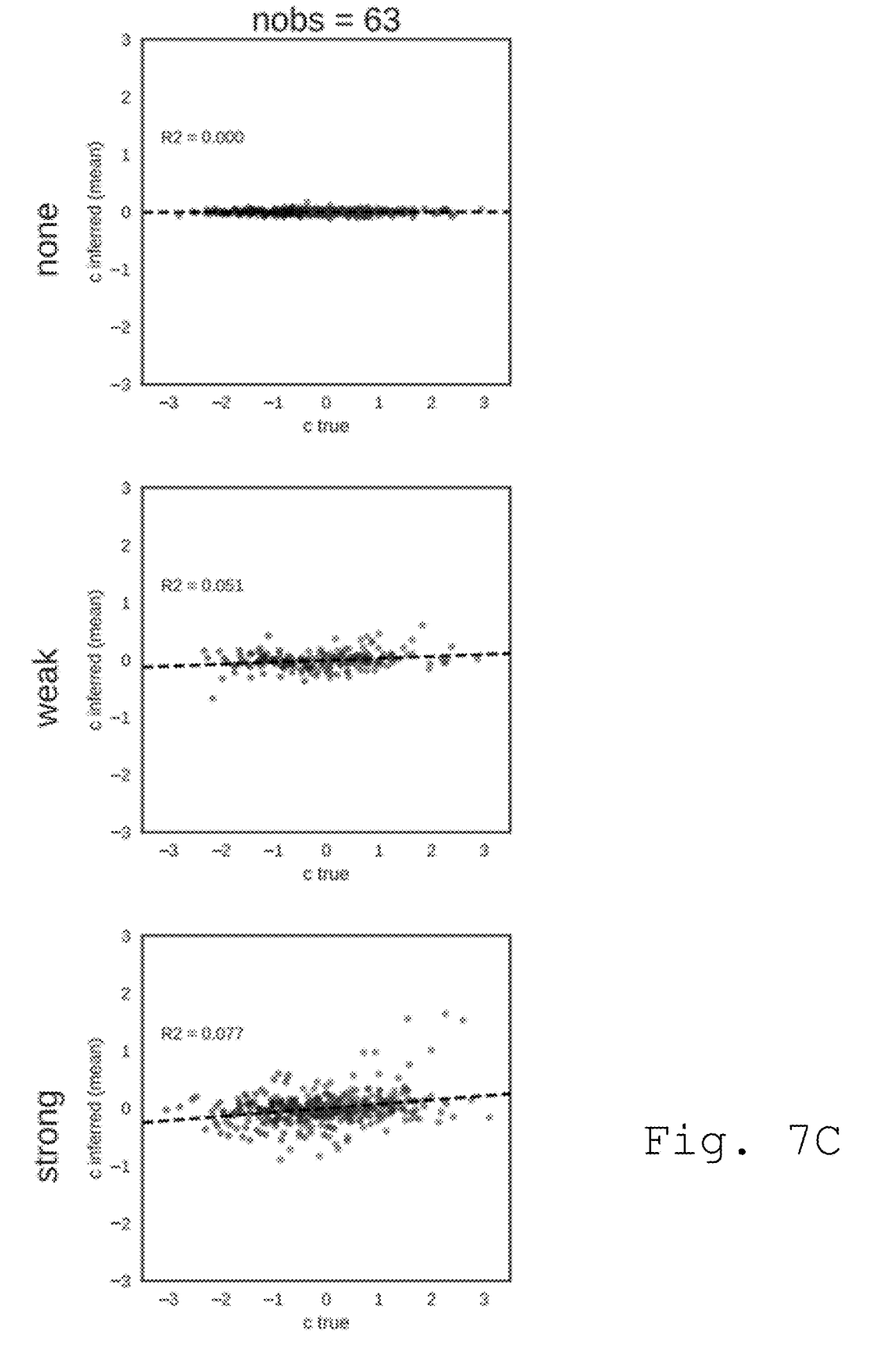

FIGS. 7A, 7B and 7C illustrate the same for nodes that are hidden. They show true and inferred node excitabilities for hidden regions. The layout is the same as FIGS. 6A, 6B and 6C. The excitability of the hidden regions is impossible to infer if there is no coupling (row none). For the strong coupling there is a certain relation of the true and inferred excitabilities (row strong) which increases with the number of observed regions.

Thus, according to the invention: with strong coupling effects, one can infer if a hidden node seizes or not, as show in FIG. 4. With strong coupling effects, also the onset time of seizing nodes can be predicted, as shown in FIG. 5. For observed nodes, excitabilities can be well inferred, especially with weak coupling effects, as shown in FIGS. 6A-6C. With strong coupling and large number of observed nodes, the excitabilities of the hidden nodes are inferred, to a certain extent, as shown in FIGS. 7A-7C.

Finally, using the partial observations of the seizure evolution in the brain network complemented by the assumption that the epileptic seizure propagates along the structural connections that can be estimated from the diffusion-weighed MRI in particular, it is possible to infer if and when are the hidden regions recruited in the seizure. To this end a data-driven dynamical model of seizure recruitment and propagation across a weighted network is used. The simple dynamical model is enriched by strong nonlinearity caused by the discontinuous changes of the node states from normal to seizing state. For the inversion of this model the Bayesian inference framework is preferentially adopted, and the parameters of the model are inferred, for example, by the Hamiltonian Monte Carlo method using the Stan software. Results of the computational experiments with the synthetic data generated by the same model show that the quality of the inference results depend on the number of observed nodes and on the connection strength. The precision of the inferred onset times increases with the number of observed nodes and with the strength of the network effects, while the capacity of the model to infer the excitabilities of the hidden nodes is limited in all studied cases. In the real epileptic seizures, these results indicate that the state of the hidden nodes during the seizure are inferred from the incomplete observations.

The invention claimed is:

1. A method for determining an onset time and/or an excitability of a brain region that is not observed as recruited or not observed as not recruited in a seizure activity of an epileptic patient brain, comprising:
   providing computerized brain networks, said networks modelling various regions of a brain and connectivity between said regions for a training cohort of epileptic patients brains and for the patient brain;
   providing data sets of observations of the state of the brain networks during epileptic seizure for the training cohort and for the patient brain, said observations defining regions in the brain networks as first regions that are observed as recruited in an epileptic seizure activity of the patient brain at an onset time,
   second regions that are observed as not recruited in the epileptic seizure activity of the patient brain, and third regions that are either not observed as recruited or not observed as not recruited in the seizure activity of the patient brain;
   providing a dynamical model of a propagation of an epileptic seizure in the brain networks, the dynamical model describing an evolution of a slow variable of a single region of the brain networks by a parametrized activation function which is a function of an excitability of the region and wherein the region onset time is defined as the time when the slow variable crosses a given threshold;
   providing a statistical model which defines the probability of generating the sets of observations of the state of the brain networks by the dynamical model;
   training the dynamical model of the propagation of an epileptic seizure using the statistical model and the data set of observations of the training cohort in order to determine an optimal set of parameters of the activation function; and
   inverting the trained dynamical model and inferring the onset time, an excitability of a third region, or both the onset time and the excitability of a third region from the onset time that is observed for the first and second regions using the statistical model.

2. The method of claim 1, wherein both the onset time and the excitability of the third region are inferred.

3. The method of claim 1, wherein the computerized brain networks are obtained from magnetic resonance neuroimaging, diffusion-weighted magnetic resonance imaging data, or both magnetic resonance neuroimaging and diffusion-weighted magnetic resonance imaging data.

4. The method of claim 1, wherein the data sets of observations of the state of the brain networks during epileptic seizure are obtained by running a seizure onset detection algorithm on intracranial electroencephalography signals and by mapping the detected onset times to the regions of the brain network.

5. The method of claim 4, wherein the seizure onset detection algorithm employs a time-frequency analysis of the intracranial electroencephalography signal.

6. The method of claim 4, wherein the mapping of the onset times detected in the intracranial electroencephalography signals onto the brain regions is based on the physical distance of the electrode contact from which the signal is recorded and the brain region.

7. The method of claim 1, wherein the parameters of the activation function of the dynamical model and the region excitabilities and onset times are inferred by an Hamiltonian Monte Carlo method.

8. The method of claim 1, wherein the dynamical model is data-driven.

9. The method of claim 1, wherein the dynamical model of a propagation of an epileptic seizure in the brain network is defined, for a brain network with n regions, by the following equation:

$$\dot{z}_i = f_q\left(c_i, \sum_{j=1}^{n} w_{ij} H(z_j - 1)\right)$$

for $i = 1, \ldots, n$ $z_i(0) = 0$ where the function $f_q: \mathbb{R} \times [0; 1] \to \mathbb{R}^+$ is the activation function,
$c_i$ is a node excitability, and
$W = (w_{ij})$ is a connectivity matrix, normalized so that $\max_i \sum_j w_{ij} = 1$ and H is the Heaviside step function representing the switch from an healthy to seizure state when the slow variable cross the threshold $z=1$.

10. The method of claim 1, wherein the statistical model is a hierarchical model built on the principles of Bayesian inference, where the top level parameters are the parameters of the activation function and the bottom level parameters are the region excitabilities.

11. The method of claim 1, wherein the statistical model includes an assumption that the excitabilities of all regions for all training data have the same prior distribution.

12. The method of claim 8, wherein the activation function $f$ is a bilinear function followed by an exponentiation, and parameters of the function are the values of the function $f$ in four specified points in $\mathbb{R} \times [0; 1]$.

13. The method one claim 1, wherein the statistical model is:

$q_{11}, q_{12} \sim \text{Normal}(0, \sigma_q)$
$q^*_{21}, q^*_{22} \sim \text{HalfNormal}(0, \sigma_q)$
$q = (q_{11}, q_{12}, q_{11} + q^*_{21}, q_{12} + q^*_{22})$
For $k = 1, \ldots, n_{seizures}$:
   $c_k \sim \text{Normal}(0, 1)$
   $t_k = P(c_k, q, W_k)$
   $\bar{t}_{k,seizing} \sim \text{Normal}(\min(t_{k,seizing}, t_{lim}), \sigma_t)$
   $t_{lim} \sim \text{Normal}(\min(t_{k,nonseizing}, t_{lim}), \sigma_t)$
   where
   $\bar{t}_{k,seizing}$ are the observed onset times of seizing nodes,
   $\sigma_q = 30$, $\sigma_t = 5$ s, $t_{lim} = \pi$s, and
   $P(c_k, q, W_k)$ represents the dynamical model, mapping the excitabilities $c_k$, parameters q, and the connectome matrix $W_k$ onto the onset times $t_k$.

14. The method of claim 5, wherein the mapping of the onset times detected in the intracranial electroencephalography signals onto the brain regions is based on the physical distance of the electrode contact from which the signal is recorded and the brain region.

15. The method of claim 2, wherein the computerized brain networks are obtained from magnetic resonance neuroimaging, diffusion-weighted magnetic resonance imaging data, or both magnetic resonance neuroimaging and diffusion-weighted magnetic resonance imaging data.

16. The method of claim 2, wherein the data sets of observations of the state of the brain networks during epileptic seizure are obtained by running a seizure onset detection algorithm on intracranial electroencephalography signals and by mapping the detected onset times to the regions of the brain network.

17. The method of claim 16, wherein the seizure onset detection algorithm employs a time-frequency analysis of the intracranial electroencephalography signal.

18. The method of claim 16, wherein the mapping of the onset times detected in the intracranial electroencephalography signals onto the brain regions is based on the physical distance of the electrode contact from which the signal is recorded and the brain region.

19. The method of claim 17, wherein the mapping of the onset times detected in the intracranial electroencephalography signals onto the brain regions is based on the physical distance of the electrode contact from which the signal is recorded and the brain region.

20. The method of claim 2, wherein the parameters of the activation function of the dynamical model and the region excitabilities and onset times are inferred by an Hamiltonian Monte Carlo method.

* * * * *